(12) United States Patent
Spada et al.

(10) Patent No.: US 7,178,703 B2
(45) Date of Patent: Feb. 20, 2007

(54) AUTOCLAVEABLE SMALL-VOLUME DROPPER BOTTLE

(75) Inventors: Lon T. Spada, Walnut, CA (US); Paul T. Butorac, Lake Forest, CA (US); Scott J. Gerondale, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 274 days.

(21) Appl. No.: 10/997,266

(22) Filed: Nov. 23, 2004

(65) Prior Publication Data

US 2006/0111680 A1     May 25, 2006

(51) Int. Cl.
*B65D 47/18* (2006.01)
(52) U.S. Cl. .................. 222/420; 222/209; 222/213; 222/562; 222/563; 604/295; 53/425
(58) Field of Classification Search ............... 222/420, 222/568, 630–633, 206, 209, 213–215, 562–563; 53/425; 604/295
See application file for complete search history.

(56) References Cited

U.S. PATENT DOCUMENTS 5,052,558 A * 10/1991 Carter ..................... 206/439
5,256,154 A * 10/1993 Liebert et al. .............. 604/199
5,487,495 A * 1/1996 Derksen ..................... 222/209
5,842,326 A * 12/1998 Wolf ........................... 53/425
5,975,381 A * 11/1999 Revenu ...................... 222/563
6,334,557 B1 * 1/2002 Yang ......................... 222/567
6,745,919 B2 * 6/2004 Moros ........................ 222/213
6,776,982 B2   8/2004 Kis et al.
2005/0159715 A1* 7/2005 Kusu .......................... 604/295

FOREIGN PATENT DOCUMENTS

EP       1449508 A1    10/2002
WO    WO2004/069679 A1  2/2003

* cited by examiner

*Primary Examiner*—Frederick C. Nicolas
(74) *Attorney, Agent, or Firm*—Walter A. Hackler

(57) ABSTRACT

A terminally sterilizable container includes a polypropylene bottle having a body with a manually squeezable sidewall and a thickness preventing water loss. The bottle body includes shoulders for providing autoclave produced pressure distribution and deformation resistance along with an elongated tips outfitted to a neck of the body and having a lumen therethrough with a drop dispensing orifice. A cap enclosed the elongated tip and includes enclosed with a nub for sealing the orifice to prevent autoclave produced pressure leaks.

15 Claims, 3 Drawing Sheets

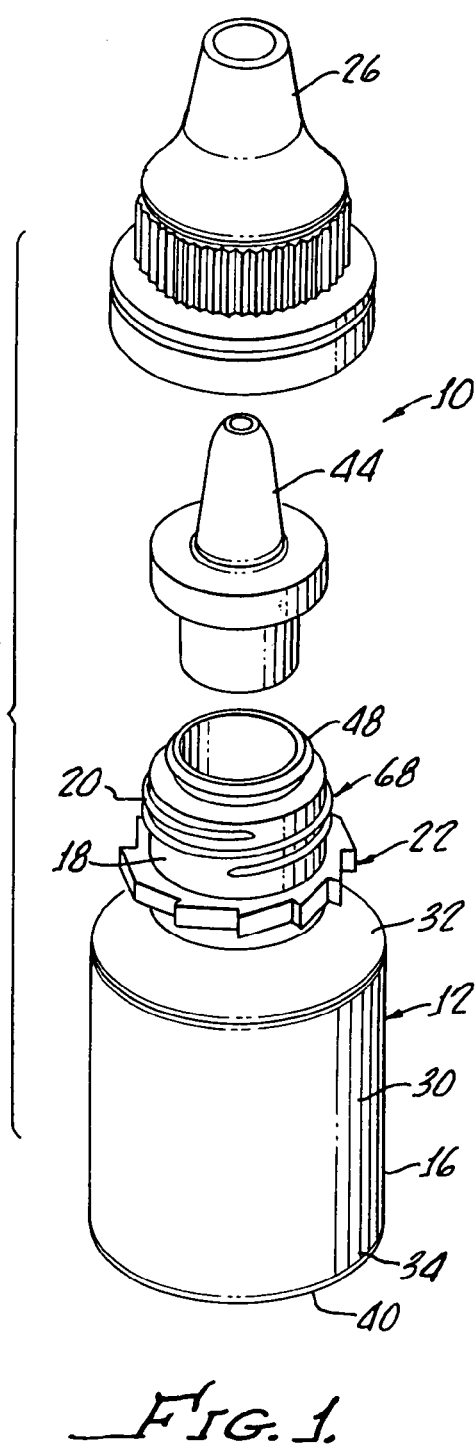
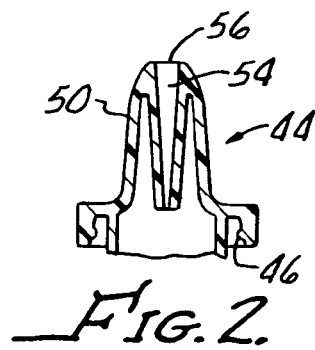
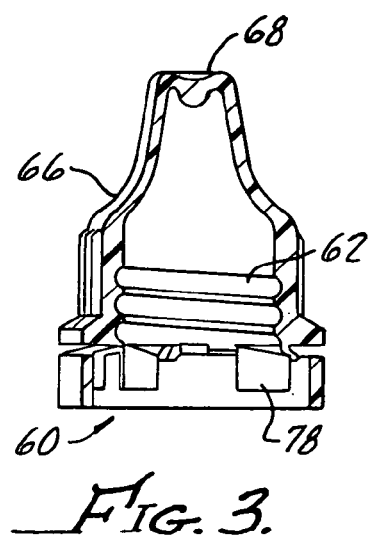
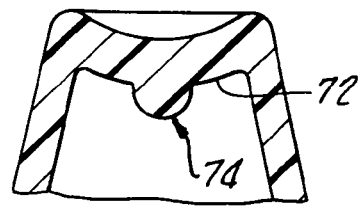
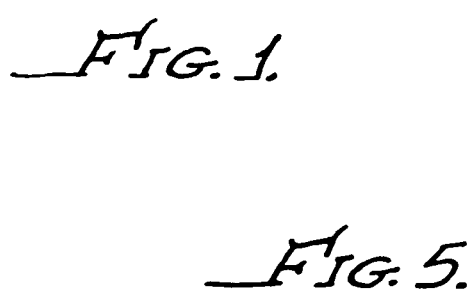

AUTOCLAVEABLE SMALL-VOLUME DROPPER BOTTLE

The present invention is generally related to dropper bottles and is more particularly directed to a squeezable autoclaveable dropper bottle.

Dropper bottles are commonly used in the dispensing of ophthalmic solutions. Preferably, the ophthalmic solutions are sterile.

With current technology, the sterility of an ophthalmic solution is assured by using sterilized individual container closure components along with aseptic filling of the sterilized product into the container. The sterility assurance level (SAL) of current processes is stated to be within $10^{-3}$ and $10^{-4}$. Some European agencies propose regulations that the SAL for ophthalmic drug should be $10^{-6}$. This SAL can be achieved by sterilizing the drug and the container closure simultaneously. This is known as terminal sterilization.

With regard to terminal sterilization, autoclave sterilization is most applicable to ophthalmic drug products because there are more drug formulations that can withstand autoclave temperatures than other methods of sterilization such as with gamma rays or ebeam.

Moist sterilization (autoclaving) is most effective terminal sterilization method against the largest variety of organisms. Dry heat sterilization requires much higher temperatures and is not as effective as autoclave sterilization against a broad range of microorganisms. Microwave and ultra high pressure are effective in select organisms and under very special circumstances.

Ophthalmic eyedroppers are typically small containers, such as, for example, 5 mL, and dispense droplets in a range of 30 microliters, ±5 microliters.

In spite of the interest in terminal sterilization, to the knowledge of the inventors there are no small-volume container closures suitable as dropper bottles that are autoclavable. This is due to the fact that polymers suitable for ophthalmic container closures that are able to withstand autoclave temperatures have a high modulus, making them difficult to squeeze for dispensing drops.

Such stiff bottles may lead to lower patient acceptability. Unfortunately, if the wall thickness of the bottle is decreased to provide a more flexible bottle, the thin wall has a higher moisture permeation which reduces the shelf life of the product. The trade off between squeezeability and water loss becomes worse as the bottle's volume gets smaller.

Another important consideration with regard to terminal sterilization is the fact that substantial internal pressure is generated inside the bottle during the autoclave cycle. This may be partially overcome by using an air-overpressure autoclave, but the design elements of the container closure must make it robust enough to maintain the seal integrity of the container closure during the sterilization of procedures.

The present invention overcomes these technical hurdles and provides for a squeezable autoclaveable dropper bottle suitable for ophthalmic formulations and sized down to about 5 ml.

SUMMARY OF THE INVENTION

A terminally sterilizable container in accordance with the present invention generally includes a polypropylene bottle having a body with a manually squeezable sidewall with a thickness preventing more than 6% water loss over a period of about 24 months. The bottle includes a threaded neck with a neck diameter smaller than a body diameter.

The body includes a top rounded shoulder below the neck and a concave bottom with a bottom rounded shoulder subtending the concave bottom and the sidewall. The top and bottle shoulder have radii providing autoclaveable produced pressure distribution and deformation resistance.

An elongated tip is provided and snap fitted to the neck the tip includes a lumen therethrough and fluid communication with the bottle and a drop-dispensing orifice.

A threaded cap engages a threaded neck and includes a cap body enclosing the elongated tip and a closed end with a nub sealing the orifice, thus preventing autoclave produced pressure leaks.

More particularly, the container in accordance with the present invention includes a top round shoulder with a surface defined by a radius of about 0.15 inches and a bottom round shoulder includes a surface defined by a radius of about 0.12 inches.

Preferably, the neck includes a peripheral ratchet and the cap includes a plurality of pawls for engaging the ratchet for providing secured sealing of the cap against the neck.

More particularly, the cap closed end may include a convex inner surface supporting the nub. This structure provides additional support for the nub in sealing the orifice.

With the use of a polypropylene bottle, a bottle volume of between about 5 ml and about 6 ml with a sidewall thickness between about 0.022 and about 0.024 inches enables manual squeezing of the bottle yet at the same time prevents substantial aqueous permeation of the sidewall.

The present invention further provides for the combination of the bottle with an autoclaveable ophthalmic formulation.

BRIEF DESCRIPTION OF THE DRAWINGS

The advantages and features of the present invention will be better understood by the following description when considered in conjunction with the accompanying drawings in which:

FIG. 1 is an exploded view of a terminally sterilizable container in accordance with the present invention generally including a polypropylene bottle having a body along with a neck, a tip, and a cap;

FIG. 2 is a cross sectional view of the tip shown in FIG. 1 more particularly illustrating a circular groove for snap fitting into the neck along with a lumen and an orifice for dropwise dispensing of an ophthalmic formulation;

FIG. 3 is a cross sectional view of the cap more clearly illustrating pawls for engagement with a neck ratchet on the bottle neck;

FIG. 4 is an enlarged cross sectional view of the cap illustrating a concave and a surface with a nub formed thereon for sealing the tip orifice;

FIG. 5 is an end view illustrating the ratchet detail on the bottleneck;

DETAILED DESCRIPTION

Figure 6:
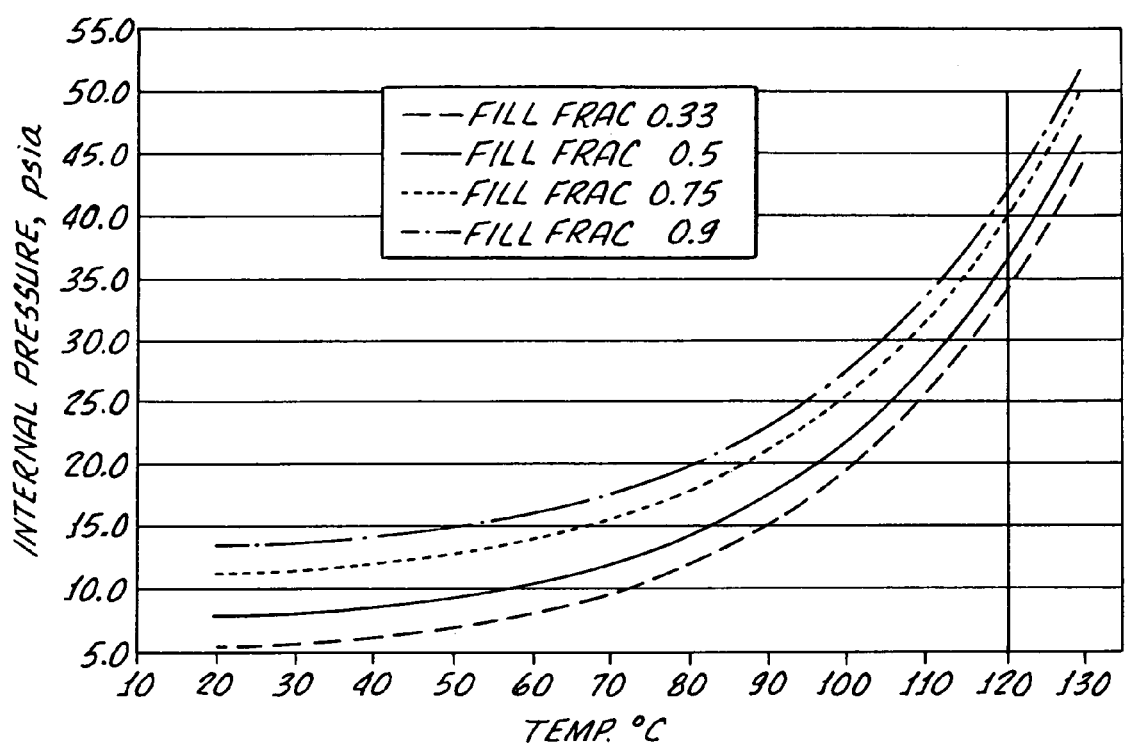
FIG. 6 is a plot of generated internal pressure vs. temperature (° C.) for autoclave bottles of the present invention.

With reference to FIG. 1, there is shown a terminally sterilizable container 10 including a polypropylene bottle 12 having a manually squeezable sidewall 16 which is formed with a thickness, as hereinafter described, which both enables manual squeezing of the bottle 12 while at the same time preventing more than about 5% water loss over a period of about 24 months.

As shown, the bottle includes a neck 18 with threads 20 molded therein along with a ratchet 22 for providing secure closure with a cap 26 in a tamper proof manner, as will be hereinafter described in greater detail.

The bottle includes a body 30 having a top rounded shoulder 32 below the neck 18 and a bottom rounded shoulder 34 subtending a concave bottle bottom 40 and the sidewall 16.

Preferably, the bottle is formed from a polypropylene provided by Phillips Marlex HLM-020 and for a 5 mL bottle has a wall thickness of between about 0.022 inches and about 0.24 inches to provide both flexibility and impermeability, as will be hereinafter discussed in greater detail.

In order to successfully autoclave the bottle and an ophthalmic formulation disposed therein under standard conditions of 121° C. for 15 minutes with an internal pressure of about 35 psig. The top rounded shoulder 32 should include a surface defined by radius of about 0.15 inches and the bottom-rounded shoulder 36 should include a surface defined by a radius of about 0.12 inches. A test example will follow.

With reference to FIG. 2, a tip 44 in accordance with the present invention which may be formed from polypropylene includes a snap 46 for fitting to a lip 48 of the neck 18 (see FIG. 1) along with an elongate portion 50 along with a lumen 54 therethrough, which communicates with the bottle body 30, and an orifice 56.

With reference to FIG. 3, there is shown a cap 60 in accordance with the present invention including threads 62 for engaging the neck threads 20 and having a cap body 66 for enclosing the elongate portion 50 of the tip 44 and further including a closed end 68 and including a convex inner surface 72 having a nub 74 molded therein for engagement and sealing the orifice 56 when the cap 60 is secured onto the neck 20. (Please see FIG. 4) This structure provides for a sufficient strength to maintain a nub 74 within the orifice to withstand autoclave produced pressure and leaking of ophthalmic formulation therepast.

In order to positively secure the cap upon tightening of the threads 20, 62 the neck 18 may include a peripheral ratchet 22, as more clearly shown in FIG. 5 and with reference to FIG. 3, the cap 60 may include a plurality of pawls 78 for engaging the ratchet 22. This additionally provides for a tamper proof cap requiring a squeezing of the cap in order to dislodge the pawls from the ratchet 22 in order to unscrew or disengage the cap 60 from the neck 18.

The cap 26 and tip 44 are produced by injection molding with Huntman P5M4-034 polypropylene resin.

Requirements for a 5 mL autoclavable container 10 closure system is shown in Table 1.

TABLE 1

| Requirements for a 5-mL Autoclaveable Container Closure System | |
|---|---|
| Property | Minimum Acceptable |
| Bottle capacity to shoulder, mL | 5.5–6.0 |
| Water Loss, 18 mo. @ 25° C./40% RH | <6% (3 mL fill vol.) |
| Squeezability | Acceptable to target market |
| Drop Size | 30 microliters |
| Drop Consistency | ±5 microliters |
| Prefill Sterilization | Autoclave/EtO |
| Terminal Sterilization Method | Autoclave |
| Leakage | 99% reliability, 95% Confidence |

Container Closure Functional Test Results

The polypropylene container 10 closure testing demonstrates that the polypropylene bottles 12 conform to the requirements listed in Table 1, and the container closure 10 does not leak, adequately protects the drug product from moisture loss and contamination, does not leach undesirable materials into the drug products, and can withstand autoclave conditions (121° C. 15 min) without leakage or deformation of the container, as well as delivering a proper drop weight acceptable by patients.

The following tests were done to demonstrate the performance of the prototype container closures 10 wall compression, moisture permeation, drop weight, European pharmacopoeia polypropylene testing, and vacuum leak. In addition, sterilization tests were completed to show the container closure can withstand the autoclave environment. These included a microbial spore reduction test, a bacterial spore kill effectiveness test and several durability tests.

Wall Compression Resistance (Squeezeability)

Polypropylene has a higher modulus than low-density polypropylene so one of the main difficulties with small polypropylene bottles is making the wall flexible enough for proper drop delivery and at the same time providing sufficient moisture barrier. On a per mil basis, polypropylene is a better moisture barrier than low-density polyethylene. The moisture barrier, however, is much more variable for polypropylene than LDPE because there are more molecular morphologies for polypropylene. Unfortunately, those that produce high moisture barrier also increase the wall stiffness.

The squeezeability of the bottle 12 was measured by several methods all of which correlated well with wall thickness. The most preferred method was done with Allergan's drop weight tester that measures the force required to deliver one drop. Each bottle was filled approximately half full with water and tested on the drop tester. The results show that a wall thickness below 0.023" produces a bottle with acceptable squeezeability, i.e. less than 0.3 lbs.

Moisture Permeability

The water loss was measured with a Mocon Permatran 3/31. The Mocon was setup and calibrated per the manufacture's instructions.

The sample containers 10 were filled with 3-mL DI water and sealed with aluminum foil glued across the mouth of the bottle (foil sealed). One to three sealed bottles were inserted into a stainless steel capture volume. Moisture loss was determined at four temperatures 25° C., 27° C., 31° C., and 35° C., and 100% relative humidity difference between the inside and outside of the bottle. The bottle's surface area and wall thickness were used to calculate the permeability constant (Pw) at each temperature. Regression analysis was used to determine the slope and intercept of an Arrhenius plot of the logarithm of the permeability constant (Pw) versus 1/T. The slope is equal to the activation energy of the permeation (Ep) divided by RT, and the intercept is equal to the permeation preexponential factor (Po). Ep and Po were then used to calculate the Pw at any temperature. The container's moisture loss at any specified temperature per unit time was calculated from the Pw and the bottle's surface area and wall thickness. The water loss was less than 6% over a period of 2 years.

Vacuum Leak Test

The container closures 10 passed a vacuum leak test conducted according to Allergan Packaging Design. Fifty units of container closure were tested with the caps 26 tightened to 5 in*lb according to ASTM D3/98.

A vacuum leak test includes sealed containers, filled with a blue dye solution, which are inverted in a vacuum chamber. White paper is placed under the bottles. A vacuum is applied to the chamber and held for a specified amount of time. At the conclusion of the test, the paper is examined for any blue stain. The cap 26 is removed from each sample and the tip area and closure threads are inspected for any blue stain.

This is an adequate test for most container closures, but these container closures must not leak under autoclave conditions, a much more stressful environment than ambient conditions.

Autoclave Pressure Durability Testing

Internal Pressure in Closed Containers

The container closure's internal pressure increases substantially when the closed container is subjected to autoclave conditions. An external pressure has to be applied to prevent leakage and damage to the container closure. This is done by injecting air with the steam into the autoclave to counterbalance the internal pressure generated inside the bottle. This is done in a special air overpressure steam autoclave. Commercial units are available, but small bench-scale units are not.

The pressure generated in the bottle and hence the sterilization cycle depends on the sterilization temperature, the ratio of headspace to fill volume, the container materials, and the solution properties. There are several factors that contribute to the increased pressure in the bottle: (1) the vapor pressure of water increases with increasing temperature. (2) The air and water vapor phase expands with temperature in the confined headspace and increases the internal pressure according to the gas laws. (3) The equilibrium concentration of dissolved gasses, such as nitrogen and oxygen, will shift to the vapor phase with increasing temperature. This can be estimated from Henry's Law. (4) The expansion of the liquid phase hyrostatically compresses the headspace vapor phase. Liquid water expands approximately 5% from 20° C. to 121° C. (5) The expansion of the container walls partially offsets the effect of items 1 through 4. This is especially true for plastic containers.

An important consequence of these considerations is that the bottle's internal pressure increases with fill volume, which can limit the maximum allowable fill volume in any container closure system.

A plot of the internal pressure versus temperature for different fill volumes is shown in FIG. 6. Container closures with fill volumes greater than 60% would be difficult to sterilized because of the high internal pressure. Most autoclaves have a maximum pressure rating of about 40 psig.

Air-Overpressure Autoclave Tests

The container closures 10 were tested to develop an overpressure steam sterilization cycle. The bottles were filled with 3-mL of distilled water. Weight loss, bottle diameter, and button depth (depth to indented bottom of bottle) were measured to assesses if there was any leakage or bottle deformation during sterilization. The bottle measurements are shown in Table 2 and the results are in Table 3.

The bottles showed no significant weight loss or dimensional changes after sterilization until the Fo was over 40. A Fo of 15 should be sufficient for terminal sterilization of ophthalmic bottles.

Lab Autoclave Testing

A VWR AccuSterilizer™ model ST113025 was modified so that air or inert gas could be automatically injected with the steam into the sterilizer chamber to compensate for the bottle's internal pressure increase. The air overpressure can be maintained throughout the sterilization cycle. The standard cycle (liquids) is 121° C. for 15 minutes.

One hundred twenty-six container closures 10 were tested in the lab autoclave. Each unit was filled with 3-mL of distilled water, the tip was inserted, and the cap was tightened to 5 in*lb bottle. Eighty-eight of the units were placed upright in the autoclave and thirty-two were inverted.

Figure 7:
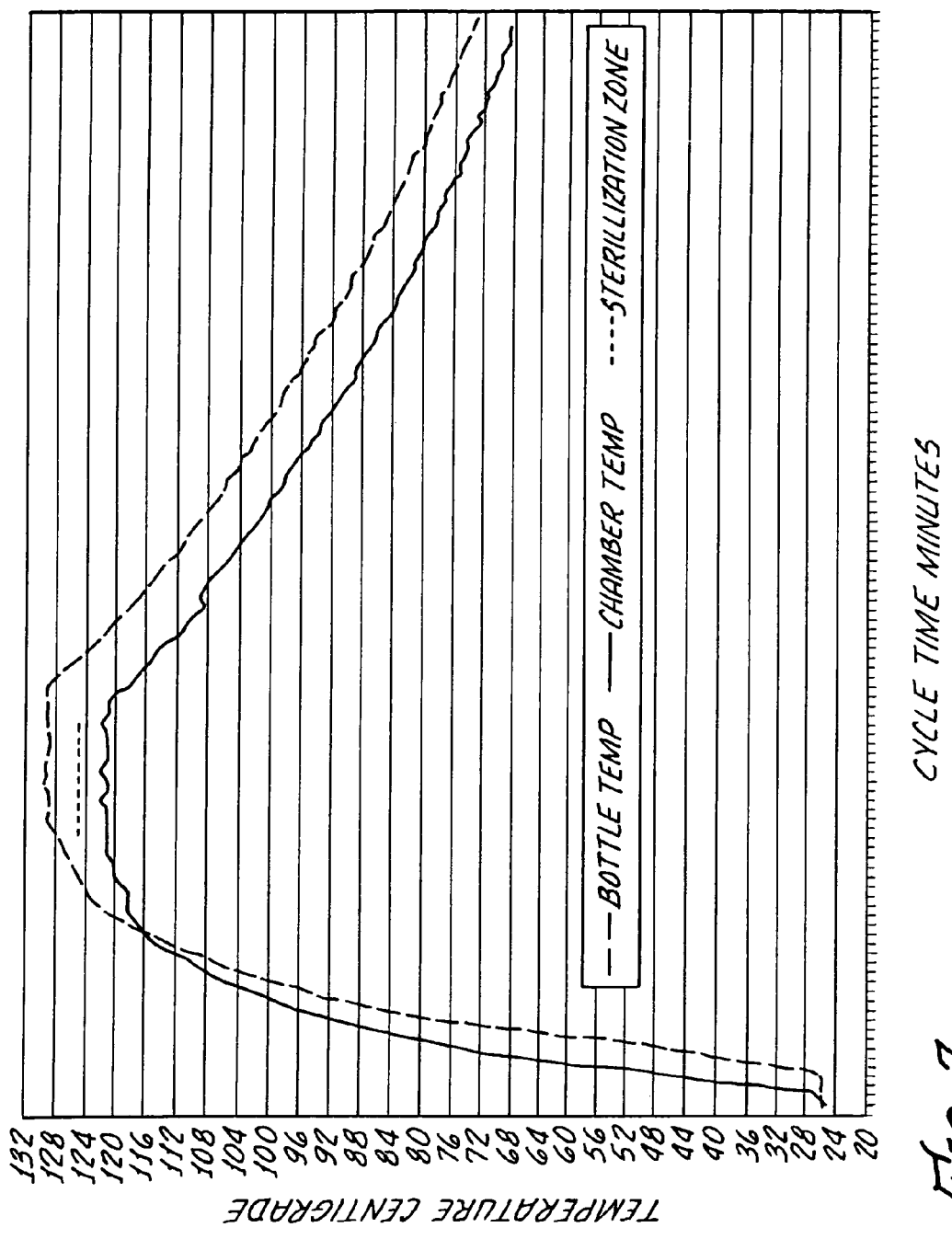
FIG. 7 is a plot of temperature (° C.) vs. cycle time (minutes) for bottles undergoing lab bench-top autoclave.

A temperature probe connected to a data logger was placed in the center of the bottles 12. A representative temperature profile for a typical run is shown in FIG. 7.

TABLE 2

Bottle Data After Autoclaving

Getinge Overpressure Sterilization Data

| Test #/Bottle | Bottle # | Initial W.t., g | Post Ster Wt., g | Detal Wt., g | Initial Diameter, mm | Post Ster Diameter, mm | Detal Diameter, mm | Initial Depth, mm | Post Ster Depth, mm | Delta Depth, mm |
|---|---|---|---|---|---|---|---|---|---|---|
| 1/602PP | 1 | 9.1 | 9.1 | 0.00 | 20.17 | 20.24 | 0.07 | 1.27 | 1.29 | 0.02 |
|  | 2 | 9.1 | 9.1 | 0.00 | 20.16 | 20.26 | 0.10 | 1.26 | 1.2 | −0.06 |
|  | 3 | 9.1 | 9.1 | 0.00 | 20.15 | 20.24 | 0.09 | 1.3 | 1.27 | −0.03 |
|  | 4 | 9.0 | 9.0 | 0.00 | 20.17 | 20.24 | 0.07 | 1.29 | 1.22 | −0.07 |
|  | 5 | 9.1 | 9.1 | 0.00 | 20.17 | 20.25 | 0.08 | 1.29 | 1.24 | −0.05 |

TABLE 3

Overpressure Autoclave Results
Getinge Overpressure Durability Results (Protocol P041)

| Bottle | Test #1 | Test #2 | Test #3 | Test #4 | Test #5 | Test #6 | Test #7 |
|---|---|---|---|---|---|---|---|
| Sterilization Temp., °C | 602PP | 603PP | 603PP | 602PP | 602PP | 602PP | 603PP |
|  | 108 | 108 | 110 | 110 | 115 | 121 | 121 |
| Sterilization Time, min | 30 | 30 | 30 | 30 | 30 | 30 | 30 |
| Pressure psi | 11.6 | 11.6 | 11.6 | 11.6 | 11.6 | 11.6 | 11.6 |
| Cooling Temp, °C | 55 | 55 | 55 | 55 | 55 | 55 | 55 |
| Fo | 2.2–2.3 | 2.2–2.3 | 3.4–3.7 | 3.4–3.8 | 10.4–11.8 | 38.7–43.8 | 40.7–45.7 |
| Result | No deformation observed | No deformation observed | No deformation observed | No deformation observed | No deformation observed | No deformation observed | No deformation observed |

Sterilization conditions were 121° C. for 15 minutes at an internal pressure of 35 psig. The bottles were checked for weight change, diameter change, leakage, and removal torque after sterilization. The container closure 10 showed no leaks in any of the units, there was no diameter increase and the average removal torque was 1.8±0.2 in*lb. There was an average weight increase of 10 mg per bottle. These results indicate that the container closure 10 is able to withstand autoclave conditions.

Market Acceptance Study

Balancing the moisture loss with squeezability is one of the major hurdles with polypropylene bottles. The prototype polypropylene bottles 12 were made with a range of wall thickness and consequently squeezability.

A market acceptance study was done in two European countries to assess the acceptability of the container closures 10. Sixty interviews were conducted. All the subjects were chronic eye drop users, averaging between 6.6 years using drops and 8.7 years using drops. Sixty-nine percent of the subjects were over age 55 and thirty-one percent were under age 55. Approximately 20% in both countries had some impairment in their hands.

Allergan's 10-mL Boston round 6-mL cylinder bottles were used as controls. The subjects were asked to bring their current bottle as well. The subjects were asked to rate the bottles on the following:

Ease of use,
ability to squeeze out drops,
ability to squeeze out one drop,
ability to remove the tamper evident seal,
and the ability to remove the cap.

The overall ranking of the bottles is shown in Table 4. Although the polypropylene bottles are firmer than their current bottle, most patients did not find them difficult to use. Both polypropylene bottles were acceptable to use and scored high in individual evaluation. There was very little difference among the bottles in their ability to "squeeze out one drop".

Overall, the patients found the polypropylene bottles acceptable to use, but they were not their first choice. They did not find them so stiff that they rated them unacceptable to use as an ophthalmic dropper bottle. A few patients liked the stiffness and felt it improved the drop control. Most patients, however, preferred to stay with their current bottle or something similar. It is apparent from this study that the bottle's 0.022 wall thickness is the upper limit of stiffness.

Most patients said it was easy to dispense one drop from the bottle 12. Twenty-five percent rated the bottle difficult to squeeze. Older patients had more difficulty controlling one drop than the younger patients. Again the older patients tended to overcompensate for the stiffness and squeezed too hard. Younger patients felt the stiffness gave them better drop control. Almost universally patients liked the locking ring closure better than the standard cello-sealed closure.

Patients had no real issues with their current bottle, so the tendency was to favor their current bottle over a new bottle. Compared to their current bottle, most found the polypropylene bottles not as acceptable as their LDPE bottles. In a forced ranking of the five bottles, the patient almost always ranked the control bottles and their current bottle higher than the polypropylene bottles. Softer was better; it was more comfortable and familiar.

TABLE 4

Results Summary for Polypropylene Bottle Market Acceptance Study

| Bottle Ranked | Overall ease of use | Squeezing out drops generally | Squeezing out just one drop |
|---|---|---|---|
| Polypropylene Bottle PP1 | 3.27 | 3.92 | 3.33 |
| Current Bottle | 2.73 | 2.81 | 2.81 |

Ranking based on a 1–5 scale with 1.0 best

Although there has been hereinabove described a specific autoclaveable small-volume dropper bottle in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A terminally sterilizable container comprising:
   a polypropylene bottle having a body with a manually squeezable sidewall with a thickness preventing more than about 6% water loss over a period of about 24 months, the bottle having a threaded neck with a neck diameter smaller than a body diameter;
   said body having a top rounded shoulder below the neck, a concave bottom with a bottom rounded shoulder subtending said concave bottom and said sidewall, the top and bottom shoulder having radii providing autoclave produced pressure distribution and deformation resistance;

an elongated tip snap fitted to said neck and having a lumen therethrough in fluid communication with said body and a drop dispensing orifice; and a threaded cap engaging said threaded neck and having a cap body enclosing said elongated tip and a closed end with a nub sealing the orifice preventing autoclave produce pressure leaks.

2. The container according to claim 1 wherein said top rounded shoulder includes a surface defined by a radius of about 0.15 inches.

3. The container according to claim 2 wherein said bottom rounded shoulder includes a surface define by a radius of about 0.12 inches.

4. The container according to claim 1 wherein said neck includes a peripheral ratchet and said caps includes a plurality of pawls engaging the ratchet.

5. The container according to claim 1 wherein the cap closed end includes a convex inner surface supporting said nub.

6. The container according to claim 1 wherein said bottle has a volume of between about 5 ml and about 6 ml.

7. The container according to claim 6 wherein the side wall therein is between about 0.022 inches and about 0.024 inches.

8. The container according to claim 7 further comprises an autoclavable ophthalmic solution disposed in said polypropylene bottle.

9. A terminally sterilizable container comprising:

a polypropylene bottle having a body with a manually squeezable sidewall with a thickness preventing more than about 6% water loss over a period of about 24 months, the bottle having a threaded neck with a neck diameter smaller than a body diameter;

said body having a top rounded shoulder below the neck, a concave bottom with a bottom rounded shoulder subtending said concave bottom and said sidewall, the top and bottom shoulder having radii providing autoclave produced pressure distribution and deformation resistance;

an elongated tip snap fitted to said neck and having a lumen therethrough in fluid communication with said body and a drop dispensing orifice;

a threaded cap engaging said threaded neck and having a cap body enclosing said elongated tip and a closed end with a nub sealing the orifice preventing autoclave produce pressure leaks; and an autoclaveable ophthalmic solution disposed in said polypropylene bottle.

10. The container according to claim 9 wherein said top rounded shoulder includes a surface defined by a radius of about 0.15 inches.

11. The container according to claim 10 wherein said bottom rounded shoulder includes a surface defined by a radius of about 0.12 inches.

12. The container according to claim 9 wherein said neck includes a peripheral ratchet and said caps includes a plurality of pawls engaging the ratchet.

13. The container according to claim 9 wherein the cap closed end includes a convex inner surface supporting said nub.

14. The container according to claim 9 wherein said bottle has a volume of between about 5 mL and about 6 mL.

15. The container according to claim 14 wherein the side wall therein is between about 0.022 inches and about 0.024 inches.

* * * * *